United States Patent
Zhao et al.

(10) Patent No.: US 11,801,500 B2
(45) Date of Patent: Oct. 31, 2023

(54) METHODS FOR PRODUCING TERTIARY AMINE CATALYSTS AND USES OF SUCH

(71) Applicant: HUNTSMAN PETROCHEMICAL LLC, The Woodlands, TX (US)

(72) Inventors: Haibo Zhao, The Woodlands, TX (US); Renjie Ji, The Woodlands, TX (US)

(73) Assignee: Huntsman Petrochemical LLC, The Woodlands, TX (US)

(*) Notice: Subject to any disclaimer, the term of this patent is extended or adjusted under 35 U.S.C. 154(b) by 533 days.

(21) Appl. No.: 17/051,938

(22) PCT Filed: May 14, 2019

(86) PCT No.: PCT/US2019/032087
§ 371 (c)(1),
(2) Date: Oct. 30, 2020

(87) PCT Pub. No.: WO2019/222127
PCT Pub. Date: Nov. 21, 2019

(65) Prior Publication Data
US 2021/0121860 A1   Apr. 29, 2021

Related U.S. Application Data

(60) Provisional application No. 62/672,159, filed on May 16, 2018.

(51) Int. Cl.
*B01J 31/02* (2006.01)
*C07C 213/08* (2006.01)

(52) U.S. Cl.
CPC ......... *B01J 31/0237* (2013.01); *C07C 213/08* (2013.01)

(58) Field of Classification Search
CPC .. B01J 31/0237; C07C 213/08; C07C 215/40; C11D 3/3723
See application file for complete search history.

(56) References Cited

U.S. PATENT DOCUMENTS

| | | |
|---|---|---|
| 8,372,304 B2 | 2/2013 | Kamada et al. |
| 8,664,445 B2 | 3/2014 | Gaspar et al. |
| 8,822,729 B2 | 9/2014 | Gaspar et al. |
| 9,382,397 B2 | 7/2016 | Gaspar et al. |
| 2002/0068244 A1 | 6/2002 | Machac, Jr. et al. |
| 2008/0271381 A1 | 11/2008 | Harashina et al. |
| 2016/0237024 A1 | 8/2016 | Gaspar et al. |
| 2017/0327690 A1 | 11/2017 | L'Oreal |

FOREIGN PATENT DOCUMENTS

| | | | |
|---|---|---|---|
| EP | 0014745 | * 9/1980 | ............ C08G 59/66 |

OTHER PUBLICATIONS

International Search Report and Written Opinion received in corresponding application No. PCT/US2019/032087 completed on Aug. 13, 2019 and dated Aug. 29, 2019.

* cited by examiner

*Primary Examiner* — Brian A McCaig
(74) *Attorney, Agent, or Firm* — HUNTSMAN PETROCHEMICAL LLC; Aleece Hayes

(57) ABSTRACT

Method for producing a tertiary amine catalyst comprising reacting a first tertiary amine having two or three hydroxyl moieties and a second tertiary amine having a halogen moiety. Also a method for producing tertiary amine catalysts comprising reacting a tertiary amine having at least two halogen moieties and either (i) a tertiary amine having at least one hydroxyl moiety, or (ii) a heterocyclic compound comprising an amine and an ether functional group.

20 Claims, No Drawings

METHODS FOR PRODUCING TERTIARY AMINE CATALYSTS AND USES OF SUCH

CROSS REFERENCE TO RELATED APPLICATIONS

This application claims benefit of PCT Application Number PCT/US2019/032087 filed May 14, 2019, which claims benefit to U.S. Provisional Patent Application No. 62/672,159 filed May 16, 2018, the entire disclosure of which is incorporated herein by reference.

STATEMENT REGARDING FEDERALLY SPONSORED RESEARCH OR DEVELOPMENT

Not applicable.

FIELD

The present disclosure generally relates to a method for producing a tertiary amine catalyst comprising reacting a first tertiary amine having two or three hydroxyl moieties and a second tertiary amine having a halogen moiety. The present disclosure is also directed to a method for producing tertiary amine catalysts comprising reacting a tertiary amine having at least two halogen moieties and either (i) a tertiary amine having at least one hydroxyl moiety or (ii) a heterocyclic compound comprising an amine and an ether functional group.

BACKGROUND

Current production routes for producing tertiary amine catalysts such as, for example, 2-({2-[2-(dimethylamino)ethoxy]ethyl}methylamino)ethan-1-ol, [2-(2-{Bis-[2-(2-dimethylamino-ethoxy)-ethyl]-amino}-ethoxy)-ethyl]-dimethylamine, and bis(N,N-2-dimethylaminoethoxyethyl)methylamine, require the use of metal catalysts and/or time-intensive separation steps which restrict how fast or efficiently the tertiary amine catalysts can be produced. See, e.g., U.S. Pat. Nos. 9,382,397, 8,664,445, and 8,822,729, and U.S. Patent Application Publication No. 2016/0237024. The production of such tertiary amine catalysts are also heavily restricted by the availability of key raw materials and/or reactants.

As demand for these tertiary amine catalysts continues to increase, so too will the need to be able to quickly and efficiently produce them. As such, there is a need for alternative methods to produce tertiary amine catalysts which require less separation steps and/or do not require the use of a metal catalyst other than an alkali metal catalyst.

DETAILED DESCRIPTION

Before explaining at least one embodiment of the present disclosure in detail, it is to be understood that the present disclosure is not limited in its application to the details of construction and the arrangement of components or steps or methodologies set forth in the following description. The present disclosure is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference and to the extent that they do not contradict the instant disclosure.

All of the compositions and/or methods disclosed herein can be made and executed without undue experimentation in light of the present disclosure. While the compositions and methods of the present disclosure have been described in terms of preferred embodiments, it will be apparent to those having ordinary skill in the art that variations may be applied to the compositions and/or methods and in the steps or sequences of steps of the methods described herein without departing from the concept, spirit, and scope of the present disclosure. All such similar substitutes and modifications apparent to those skilled in the art are deemed to be within the spirit, scope, and concept of the present disclosure.

As utilized in accordance with the present disclosure, the following terms, unless otherwise indicated, shall be understood to have the following meanings.

The use of the word "a" or "an", when used in conjunction with the term "comprising", "including", "having", or "containing" (or variations of such terms) may mean "one", but it is also consistent with the meaning of "one or more", "at least one", and "one or more than one".

The use of the term "or" is used to mean "and/or" unless clearly indicated to refer solely to alternatives and only if the alternatives are mutually exclusive.

Throughout this disclosure, the term "about" is used to indicate that a value includes the inherent variation of error for the quantifying device, mechanism, or method, or the inherent variation that exists among the subject(s) to be measured. For example, but not by way of limitation, when the term "about" is used, the designated value to which it refers may vary by plus or minus ten percent, or nine percent, or eight percent, or seven percent, or six percent, or five percent, or four percent, or three percent, or two percent, or one percent, or one or more fractions therebetween.

The use of "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it refers. In addition, the quantities of 100/1000 are not to be considered as limiting since lower or higher limits may also produce satisfactory results.

In addition, the phrase "at least one of X, Y, and Z" will be understood to include X alone, Y alone, and Z alone, as well as any combination of X, Y, and Z. Likewise, the phrase "at least one of X and Y" will be understood to include X alone, Y alone, as well as any combination of X and Y. Additionally, it is to be understood that the phrase "at least one of" can be used with any number of components and have the similar meanings as set forth above.

The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The phrases "or combinations thereof" and "and combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more items or terms such as BB, AAA, CC, AABB, AACC, ABCCCC, CBBAAA, CABBB, and so forth. The skilled artisan will understand that typically there is no limit on the number of items or terms in any combination, unless otherwise apparent from the context. In the same light, the term "and combinations thereof" when used with the phrase "selected from the group consisting of" refers to all permutations and combinations of the listed items preceding the phrase.

The phrases "in one embodiment", "in an embodiment", "according to one embodiment", and the like generally mean the particular feature, structure, or characteristic following the phrase is included in at least one embodiment of the present disclosure and may be included in more than one embodiment of the present disclosure. Importantly, such phrases are non-limiting and do not necessarily refer to the same embodiment but, of course, can refer to one or more preceding and/or succeeding embodiments. For example, in the appended claims, any of the claimed embodiments can be used in any combination.

As used herein, the terms "% by weight", "wt %", "weight percentage", or "percentage by weight" are used interchangeably.

The phrase "substantially free" shall be used herein to mean present in an amount less than 1 weight percent, or less than 0.1 weight percent, or less than 0.01 weight percent, or alternatively less than 0.001 weight percent, based on the total weight of the referenced composition.

The term "alkyl" is inclusive of both straight chain and branched chain groups and of cyclic groups. In some embodiments, the alkyl group may have up to 40 carbons (in some embodiments up to 30, 20, 15, 12, 10, 8, 7, 6, 5, 4, 3, 2, or 1 carbons) unless otherwise specified. Cyclic groups can be monocyclic and in some embodiments, can have from 3 to 10 carbon atoms.

Unless otherwise specified, the reaction conditions disclosed herein are intended to be at atmospheric pressure, i.e., about 101 kPa.

It shall also be understood that the expression "room temperature", if used herein, is to mean the temperature of the surrounding work environment (e.g., the temperature of the area, building or room where the formation of tertiary amine catalysts occurs), exclusive of any temperature changes that occur as a result of the direct application of heat to the reactants before, during, or after reacting such. Room temperature is typically between about 10° C. and about 30° C.

According to one aspect, the present disclosure is directed to a method for producing a tertiary amine catalyst comprising reacting a first tertiary amine having two or three hydroxyl moieties and a second tertiary amine having a halogen moiety.

More particularly, the present disclosure is directed to a method for producing a tertiary amine catalyst comprising reacting:

(i) a first tertiary amine represented by formula (I):

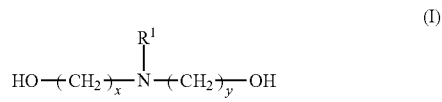

wherein $R^1$ is selected from a methyl group, an ethyl group, an iso-propyl group, an n-propyl group, and a hydroxyalkyl group selected from a hydroxymethyl group, a hydroxyethyl group, a hydroxypropyl group, and a hydroxyisopropyl group, and x and y each independently range from 1 to 4; and (ii) a second tertiary amine represented by formula (II):

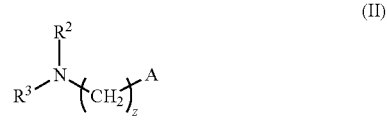

wherein $R^2$ and $R^3$ are (i) each independently selected from a methyl group, an ethyl group, an iso-propyl group, an n-propyl group, and

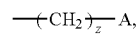

or (ii) linked to form a ring structure having 2 to 8 carbon atoms; z is in a range of from 1 to 4; and A is a halogen.

In one embodiment, A is selected from chlorine, bromine, and iodine. In a preferred embodiment, A is chlorine.

In one particular embodiment, the first tertiary amine is methyl diethanolamine ("MDEA"), which is represented by formula (I) when $R^1$ is a methyl group and each of x and y is 2.

In another particular embodiment, the second tertiary amine is 2-dimethylaminoethyl chloride, which is represented by formula (II) when $R^2$ and $R^3$ are each a methyl group, z is 2, and A is Cl. 2-dimethylaminoethyl chloride is usually found in the presence of a hydrochloride salt, which is implicit when referring to 2-dimethylaminoethyl chloride unless otherwise stated herein.

In one particular embodiment, the 2-dimethylaminoethyl chloride is first produced by reacting dimethyl ethanolamine ("DMEA") and thionyl chloride.

In still a further embodiment, the method for producing a tertiary amine catalyst comprises reacting (i) a first tertiary amine represented by formula (I) wherein $R^1$ is a methyl group and each of x and y is 2, and (ii) a second tertiary amine represented by formula (II) wherein $R^2$ and $R^3$ are each a methyl group and z is 2, such that the reaction of the first tertiary amine and the second tertiary amine produces a tertiary amine catalyst comprising at least one of formulas (III) and (IV):

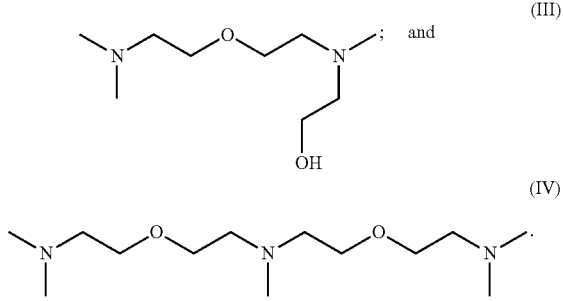

Formula (III) is representative of 2-({2-[2-(dimethylamino)ethoxy]ethyl}-methylamino)ethan-1-ol and formula (IV) is representative of bis(N,N-2-dimethylaminoethoxyethyl)methylamine.

In an alternative embodiment, the method for producing a tertiary amine catalyst comprises reacting (i) a first tertiary amine represented by formula (I) wherein $R^1$ is a hydroxyethyl group and each of x and y is 2, and (ii) a second tertiary amine represented by formula (II) wherein $R^2$ and $R^3$ are each a methyl group and z is 2, such that the reaction of the first tertiary amine and the second tertiary amine produces a tertiary amine catalyst comprising at least one of formulas (V), (VI), and (VII):

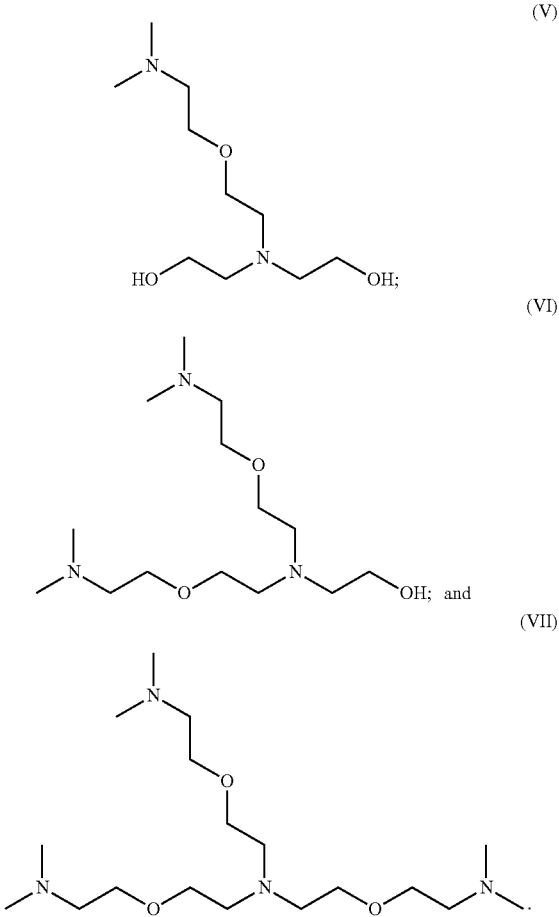

The step of reacting the first tertiary amine and the second tertiary amine comprises heating the first tertiary amine and the second tertiary amine for a time and temperature sufficient to produce the tertiary amine catalyst as described herein. In one embodiment, the first tertiary amine and the second tertiary amine are reacted at a temperature in a range of from about 0 to about 150° C. and at a pressure ranging from about 1 atm to about 10 atm.

In one particular embodiment, the first tertiary amine and the second tertiary amine are reacted at a temperature ranging from 0 to 150° C., or from 60 to 140° C., or from 80 to 120° C. at 1 atm for a time ranging from 0.5 hour to 24 hours, or from about 4 hours to about 20 hours, or from 6 hours to 16 hours.

The molar ratio of the first tertiary amine reacted with the second tertiary amine is in a range of from about 1:2 to about 1:10, or from about 1:2 to 1:4, or from about 1:2 to 1:3 of the first tertiary amine to the second tertiary amine.

In one embodiment, the first tertiary amine and the second tertiary amine are reacted in the presence of a base, wherein the base is any alkali metal hydroxide or methoxide. Non-limiting examples of the base include sodium hydroxide, potassium hydroxide, sodium methoxide, and potassium methoxide.

The amount of base used in the presently disclosed method is in a range of from about 2.2:1 to about 1:1 or from about 2.2:1 to about 1.7:1 based on the molar ratio of the base to the second tertiary amine.

In one embodiment, the method for producing the tertiary amine catalyst is substantially free of metal catalysts other than an alkali metal catalyst.

In another embodiment, the method for producing the tertiary amine catalyst comprises first mixing the first tertiary amine and second tertiary amine to form a reaction mixture, and then reacting the reaction mixture to produce the tertiary amine catalyst.

In another aspect, the present disclosure is directed to a method for producing a tertiary amine catalyst comprising reacting a tertiary amine having at least two halogen moieties and a tertiary amine having at least one hydroxyl moiety.

In one embodiment, the tertiary amine having at least two halogen moieties is represented by formula (VIII):

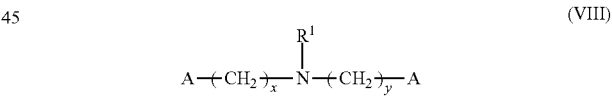

wherein $R^1$ is selected from a methyl group, an ethyl group, an iso-propyl group, an n-propyl group, a hydroxyalkyl group selected from a hydroxymethyl group, a hydroxyethyl group, a hydroxypropyl group, and a hydroxyisopropyl group, and

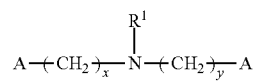

and wherein x, y, and z each range from 1 to 4, and A is a halogen.

In one embodiment, A is selected from chlorine, bromine, and iodine. In one preferred embodiment, A is chlorine.

In one particular embodiment, the tertiary amine having at least two halogen moieties is N,N-Bis(2-chloroethyl)methylamine. N,N-Bis(2-chloroethyl)methylamine is usually found in the presence of a hydrochloride salt, which is implicit when referring to N,N-Bis(2-chloroethyl)methylamine unless otherwise stated herein. N,N-Bis(2-chloroethyl)methylamine is represented by formula (VIII) when A is Cl, each of x and y is 2, and R¹ is a methyl group.

In one embodiment, the N,N-Bis(2-chloroethyl)methylamine is formed by reacting methyl diethanolamine ("MDEA") and thionyl chloride.

The tertiary amine having at least one hydroxyl moiety is represented by formula (IX):

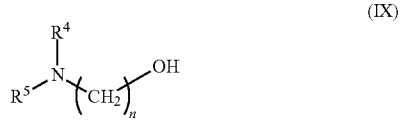

(IX)

wherein R⁴ and R⁵ are independently selected from a methyl group, an ethyl group, an iso-propyl group, and an n-propyl group, and n ranges from 1 to 4.

In one particular embodiment, the tertiary amine having at least one hydroxyl moiety is dimethyl ethanolamine, which is represented by formula (IX) when R⁴ and R⁵ are each a methyl group and n is 2.

In another embodiment, the tertiary amine having at least two halogen moieties is N,N-Bis(2-chloroethyl)methylamine and the tertiary amine having at least one hydroxyl moiety is dimethyl ethanolamine such that, when reacted, bis(N,N-2-dimethylaminoethoxyethyl)methylamine (corresponding to formula (IV)) is formed:

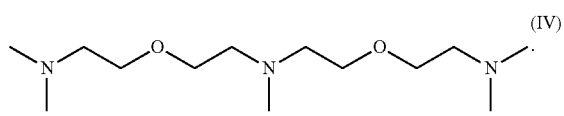

(IV)

The step of reacting (i) the tertiary amine having at least two halogen moieties and (ii) the tertiary amine having at least one hydroxyl moiety comprises heating the reactants for a time and temperature sufficient to produce the tertiary amine catalyst as described herein. In one embodiment, the tertiary amine having at least two halogen moieties and the tertiary amine having at least one hydroxyl moiety are reacted at a temperature in a range of from about 0 to about 150° C. and at a pressure ranging from about 1 atm to about 10 atm.

In one particular embodiment, the tertiary amine having at least two halogen moieties and the tertiary amine having at least one hydroxyl moiety are reacted at a temperature ranging from 0 to 150° C., or from 60 to 140° C., or from 80 to 120° C. at 1 atm for a time ranging from 0.5 hour to 24 hours, or from about 4 hours to about 20 hours, or from about 6 hours to about 16 hours.

The molar ratio of the tertiary amine having at least two halogen moieties reacted with the tertiary amine having at least one hydroxyl moiety is in a range of from about 1:2 to about 1:10, or from about 1:2 to 1:4, or from about 1:2 to 1:3 of the tertiary amine having at least two halogen moieties to the tertiary amine having at least one hydroxyl moiety.

In one embodiment, the tertiary amine having at least two halogen moieties and the tertiary amine having at least one hydroxyl moiety are reacted in the presence of a base, wherein the base is any alkali metal hydroxide or methoxide. Non-limiting examples of the base include sodium hydroxide, potassium hydroxide, sodium methoxide, and potassium methoxide.

The amount of base used in the presently disclosed method is in a range of from about 2:1 to 1:1 or from about 1.1:1 to 1:1 based on the molar ratio of the base to the tertiary amine having at least one hydroxyl moiety.

In one embodiment, the method for producing the tertiary amine catalyst is substantially free of metal catalysts other than an alkali metal catalyst.

In another embodiment, the method for producing the tertiary amine catalyst comprises first mixing the tertiary amine having at least two halogen moieties and the tertiary amine having at least one hydroxyl moiety to form a reaction mixture, and then reacting the reaction mixture to produce the tertiary amine catalyst.

In yet another aspect, the present disclosure is directed to a method for producing a tertiary amine catalyst comprising reacting a tertiary amine having at least two halogen moieties (as previously described herein) and a heterocyclic compound comprising an amine and an ether functional group.

In one embodiment, the heterocyclic compound is morpholine.

In another embodiment, the tertiary amine having at least two halogen moieties is N,N-Bis(2-chloroethyl)methylamine and the heterocyclic compound is morpholine such that, when reacted, the following tertiary amine catalyst represented by formula (X) is formed:

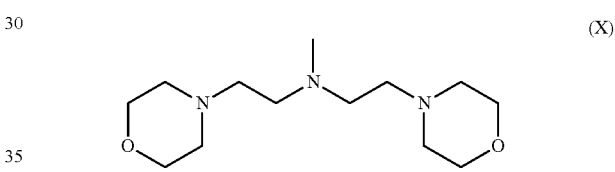

(X)

The tertiary amine having at least two halogen moieties and the heterocyclic compound are reacted at a time and temperature sufficient to produce the tertiary amine catalyst as described herein. In one embodiment, the tertiary amine having at least two halogen moieties and the heterocyclic compound are reacted at a temperature in a range of from about 0 to about 150° C. and at a pressure ranging from about 1 atm to about 10 atm.

In one particular embodiment, the tertiary amine having at least two halogen moieties and the heterocyclic compound are reacted at a temperature ranging from 0 to 150° C., or from 20 to 140° C., or from 40 to 120° C. at 1 atm for a time ranging from 0.5 hour to 24 hours, or from about 1 hour to about 10 hours, or from about 2 hours to about 6 hours.

The molar ratio of the tertiary amine having at least two halogen moieties reacted with the heterocylic compound is in a range of from about 1:2 to about 1:10, or from about 1:2 to 1:4, or from about 1:2 to 1:3 of the tertiary amine having at least two halogen moieties to the heterocyclic compound.

In one embodiment, the tertiary amine having at least two halogen moieties and the heterocyclic compound are reacted in the presence of a base, wherein the base is any alkali metal hydroxide or methoxide. Non-limiting examples of the base include sodium hydroxide, potassium hydroxide, sodium methoxide, and potassium methoxide. In another embodiment, the tertiary amine having at least two halogen moieties and heterocyclic compound are reacted in the presence of excess of heterocyclic compound.

The amount of base that can be used in the presently disclosed method is in a range of form about 10:1 to 1:1 based on the molar ratio of base to the tertiary amine having at least two halogen moieties.

In one embodiment, the method for producing the tertiary amine catalyst is substantially free of metal catalysts other than an alkali metal catalyst.

In another embodiment, the method for producing the tertiary amine catalyst comprises first mixing the tertiary amine having at least two halogen moieties and the heterocyclic compound to form a reaction mixture, and then reacting the reaction mixture to produce the tertiary amine catalyst.

In a further aspect, the present disclosure is directed to a method for producing a tertiary amine catalyst comprising reacting piperazine with a tertiary amine having formula (II) as set forth herein.

In one embodiment, the tertiary amine reacted with piperazine is 2-dimethylaminoethyl chloride, such that the resulting tertiary amine catalyst is 1-[2-(Dimethylamino) ethyl]piperazine represented by formula (XI):

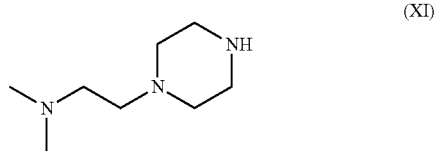

(XI)

The tertiary amine catalysts produced by the aforementioned methods, including formulas (III)-(VII), (X), and (XI), can be used in catalyst systems for polyurethane and/or polyurea foam production. In particular, formula (III) is representative of 2-({2-[2-(dimethylamino)ethoxy]ethyl}methylamino)ethan-1-ol, formula (IV) is representative of bis(N,N-2-dimethylaminoethoxyethyl)methylamine, and formula (VII) is representative of [2-(2-{Bis-[2-(2-dimethylamino-ethoxy)-ethyl]-amino}-ethoxy)-ethyl]-dimethyl-amine, which are described in, for example, U.S. Pat. No. 9,382,397 as suitable catalysts for the formation of polyurethane or polyurea foam material.

In one particular embodiment the tertiary amine catalysts produced by one or more of the presently disclosed methods can generally be used to provide a polyurethane or polyurea foamed material by (i) mixing a polyisocyanate component, an isocyanate-reactive component, water, and the tertiary amine catalysts as described herein, and (ii) reacting the mixture at a time and temperature sufficient to form a polyurethane or polyurea foam.

The polyisocyanate component may comprise any number of polyisocyanates, including but not limited to, toluene diisocyanates (TDI), diphenylmethane diisocyanate (MDI)-type polyisocyanates, and prepolymers of these isocyanates, aliphatic isocyanates such as IPDI (isophoronediisocyanate), and hexamethylene diisocyanate and derivatives thereof In case diphenylmethane diisocyanate (also known as methylene diphenyl diisocyanate, and referred to as MDI) is used, the diphenylmethane diisocyanate (MDI) can be in the form of its 2,4'-, 2,2'-, and 4,4'-isomers and mixtures thereof, the mixtures of diphenylmethane diisocyanates (MDI) and oligomers thereof known in the art as "crude" or polymeric MDI (polymethylene polyphenylene polyisocyanates) having an isocyanate functionality of greater than 2, or any of their derivatives having a urethane, isocyanurate, allophonate, biuret, uretonimine, uretdione and/or iminooxadiazinedione groups and mixtures of the same.

Non-limiting examples of other suitable polyisocyanates are tolylene diisocyanate (also known as toluene diisocyanate, and referred to as TDI), such as 2,4-TDI and 2,6-TDI in any suitable isomer mixture, hexamethylene diisocyanate (HMDI or HDI), isophorone diisocyanate (IPDI), butylene diisocyanate, trimethylhexamethylene diisocyanate, di(isocyanatocyclohexyl)methane, e.g. 4,4'-diisocyanatodicyclohexylmethane (H12MDI), isocyanatomethyl-1,8-octane diisocyanate and tetramethylxylene diisocyanate (TMXDI), 1,5-naphtalenediisocyanate (NDI), p-phenylenediisocyanate (PPDI), 1,4-cyclohexanediisocyanate (CDI), tolidine diisocyanate (TODI), any suitable mixture of these polyisocyanates, and any suitable mixture of one or more of these polyisocyanates with MDI in the form of its 2,4'-, 2,2'- and 4,4'-isomers and mixtures thereof, the mixtures of diphenylmethane diisocyanates (MDI) and oligomers thereof.

The isocyanate-reactive component can be any polyalcohol. Typically polyether polyols or polyester polyols are used.

Non-limiting examples of the polyether polyols are polyethylene glycol, polypropylene glycol, polypropylene glycol-ethylene glycol copolymer, polytetramethylene glycol, polyhexamethylene glycol, polyheptamethylene glycol, polydecamethylene glycol, and polyether polyols obtained by ring-opening copolymerisation of alkylene oxides, such as ethylene oxide and/or propylene oxide, with isocyanate-reactive initiators of functionality 2 to 8. The functionality of the isocyanate-reactive initiators is to be understood as the number of isocyanate-reactive hydrogen atoms per molecule initiator.

The polyester polyol can be a polyester diol obtained by reacting a polyhydric alcohol and a polybasic acid. Non-limiting examples of such polyols include ethylene glycol, polyethylene glycol, tetramethylene glycol, polytetramethylene glycol, 1,6-hexanediol, 3-methyl-1,5-pentanediol, 1,9-nonanediol, 2-methyl-1,8-octanediol, and the like can be given. As examples of the polybasic acid, phthalic acid, dimer acid, isophthalic acid, terephthalic acid, maleic acid, fumaric acid, adipic acid, sebacic acid, and the like can be given.

EXAMPLES

Examples are provided below. However, the present disclosure is to be understood to not be limited in its application to the specific experiments, results, and laboratory procedures disclosed herein below. Rather, the Examples are simply provided as one of various embodiments and are meant to be exemplary and not exhaustive.

Example 1

Potassium hydroxide (flake, 15.4 g, 0.234 mol) was added to a solution of methyl diethanolamine ("MDEA") (16.5 g, 0.138 mol) in toluene (90 g). The mixture of such was heated to reflux with stirring. After reflux for 1 hrs, most of the potassium hydroxide flake had dissolved and a cream white solution was obtained. The solution was then cooled to 75° C., whereupon 2-dimethylaminoethyl chloride (20 g, 0.138 mol) was added in two approximately equal portions over a 15 minute period. The mixture was refluxed for 12 hours after the chloride addition had been completed. During the reaction, the reaction temperature declined from 112° C. to 93° C. After cooling to room temperature, potassium chloride formed very fine crystal, the reddish brown liquid was decanted from salts, the solid residue was washed three times with toluene (30 g) and the washings combined with the liquid products. After removing toluene with vacuum strip, the GC analysis showed that the product contained 63.1% of 2-({2-[2-(dimethylamino)ethoxy]ethyl}methylamino)ethan-1-ol, 15.2% of bis(N,N-2-dimethylaminoethoxyethyl)methylamine, and 3% residual MDEA by weight.

Example 2

Sodium hydroxide (flake, 11.8 g, 0.286 mol) was added to a solution of MDEA (13.7 g, 0.115 mol) in toluene (150 g). The mixture of such was refluxed with stirring. Water was removed through Dean-Stark trap over 1 hour. Most of the sodium hydroxide dissolved after 10 minutes and a cream white solution was obtained. A solution of 2-dimethylaminoethyl chloride (20 g, 0.138 mol) in water (8 g) was added drop-wise over 14 minutes, during which the temperature of the reactor declined from 112° C. to 102° C. After reflux for 12 hours, the reaction product was cooled to room temperature and the reddish brown liquid was decanted from sodium chloride salts, the solid residue was washed three times with toluene (40 g) and the washings combined with the liquid products. After removing toluene with vacuum strip, the GC analysis showed that the product contained 67.3% of 2-({2-[2-(dimethylamino)ethoxy]ethyl}methylamino)ethan-1-ol, 15.1% of bis(N,N-2-dimethylaminoethoxyethyl)methylamine, and 17.6% residual MDEA by weight.

Example 3

The apparatus and procedure of example 2 were repeated using identical quantities of all reactants except that the 20 g (0.138 mol) of 2-dimethylaminoethyl chloride was substituted for 31.9 g (0.155 mol) 70% crude 2-dimethylaminoethyl chloride hydrochloride solution. After removing toluene with vacuum strip, the GC analysis showed that the product contained 62.7% of 2-({2-[2-(dimethylamino)ethoxy]ethyl}methylamino)ethan-1-ol, 7.2% of bis(N,N-2-dimethylaminoethoxyethyl)methylamine, and 17.8% residual MDEA by weight.

Example 4

The apparatus and procedure of example 3 were repeated using identical quantities of all reactants except that the 31.9 g (0.155 mol) of 70% crude 2-dimethylaminoethyl chloride solution was substituted for 28.4 g (0.138 mol) 70% 2-dimethylaminoethyl chloride hydrochloride solution. After removing toluene with vacuum strip, the GC analysis showed that the product contained 66.3% of 2-({2-[2-(dimethylamino)ethoxy]ethyl}methylamino)ethan-1-ol, 8% of bis(N,N-2-dimethylaminoethoxyethyl)methylamine, and 22% residual MDEA by weight.

Example 5

Sodium hydroxide (flake, 12.3 g, 0.298 mol) was added to a solution of MDEA (16.5 g, 0.138 mol) in toluene (170 g). The mixture of such was refluxed with stirring. Water was removed through Dean-Stark trap over 1 hour. A cream white solution was obtained after refluxing for 10 minutes. A solution of 2-dimethylaminoethyl chloride (33.2 g, 70% solution, 0.161 mol) was added drop-wise over 17 minutes, during which the temperature of the reactor declined from 112° C. to 101° C. After reflux for 6 hours, the GC analysis showed that the product contained 54% of 2-({2-[2-(dimethylamino)ethoxy]ethyl}methylamino)ethan-1-ol, 4.6% of bis(N,N-2-dimethylaminoethoxyethyl)methylamine, and 31.3% residual MDEA by weight.

The product was then subject to reflux for another 6 hours and then cooled to room temperature. The reddish brown liquid reaction product was decanted from salts, the solid residue was washed three times with toluene (40 g) and the washings combined with the liquid products. After removing toluene with vacuum strip, the GC analysis showed that the product contained 56.3% of 2-({2-[2-(dimethylamino)ethoxy]ethyl}methylamino)ethan-1-ol, 5.1% of bis(N,N-2-dimethylaminoethoxyethyl)methylamine, and 29% residual MDEA by weight.

Example 6

Sodium hydroxide (flake, 848 g, 20.56 mol) was added to a solution of MDEA (900 g, 7.56 mol) in toluene (1430 g). The mixture of such was then refluxed with stirring. Water was removed through Dean-Stark trap over 7 hours. A solution of 2-dimethylaminoethyl chloride (1940 g, 70% solution, 9.44 mol) was then added drop-wise over 3 hour, during which the temperature of the reactor declined to 99° C. The reaction was continued for 12 hours after the addition of the chloride was complete. After being cooled to 50° C., the reaction product was filtered through a Buchner funnel, the residue was washed three times with toluene (400 g), and the washings combined with the liquid products. After removing toluene with vacuum strip, the GC analysis showed that the product contained 44.7% of 2-({2-[2-(dimethylamino)ethoxy]ethyl}methylamino)ethan-1-ol, 12.6% of bis(N,N-2-dimethylaminoethoxyethyl)methylamine, and 22.2% residual MDEA by weight.

Example 7

Sodium hydroxide (flake, 313 g, 7.6 mol) was added to a solution of MDEA (341.5 g, 2.87 mol) in toluene (2500 g). The mixture of such was then refluxed with stirring. Water was removed through Dean-Stark trap over 5 hrs. A solution of crude 2-dimethylaminoethyl chloride (710 g, 70% solution, 3.45 mol) in water was added drop-wise over 2 hours, during which the temperature of the reactor declined from 112° C. to 99° C. The reaction continued for 12 hours after the addition of the chloride was complete. After being cooled to 50° C., the reaction product was filtered through a Buchner funnel, the residue was washed three times with toluene (400 g), and the washings combined with the liquid products. After removing toluene with vacuum strip, the GC analysis showed that the product contained 64.8% of 2-({2-[2-(dimethylamino)ethoxy]ethyl}methylamino)ethan-1-ol, 16.6% of bis(N,N-2-dimethylaminoethoxyethyl)methylamine, and 8.5% residual MDEA by weight.

Example 8

Sodium hydroxide (flake, 11.5 g, 0.284 mol) was added to a solution of MDEA (13.7 g, 0.115 mol) in toluene (150 g). The mixture of such was then heated to reflux with stirring. After reflux for 1 hour, most of the sodium hydroxide flake had dissolved and a cream white solution was obtained. The solution was allowed to cool to 75° C., whereupon 2-dimethylaminoethyl chloride (20 g, 0.138 mol) was added in two approximately equal portions over 15 minutes. The mixture was refluxed for 12 hours after the chloride addition was complete. During the reaction, the reaction temperature declined from 112° C. to 101° C. After cooling to room temperature, the reddish brown liquid reaction product was decanted from salts, the solid residue was washed three times with toluene (30 g), and the washings combined with the liquid products. After removing toluene with vacuum strip, the GC analysis showed that the product contained 46.4% of 2-({2-[2-(dimethylamino)ethoxy] ethyl}methylamino)ethan-1-ol, 15.9% of bis(N,N-2-dimethylaminoethoxyethyl)methylamine, and 35% residual MDEA by weight.

Example 9

Sodium hydroxide (flake, 19.6 g, 0.485 mol) was added to a solution of MDEA (14.7 g, 0.123 mol) in toluene (170 g). The mixture of such was heated to reflux with stirring. After reflux for 1 hour, most of the sodium hydroxide flake had dissolved and a cream white solution was obtained. The solution was allowed to cool to 75° C., whereupon 2-dimethylaminoethyl chloride (35.5 g, 0.246 mol) was added in two approximately equal portions over 15 minutes. The mixture was refluxed for 12 hours after the chloride addition was complete. During the reaction, the reaction temperature declined to 101° C. After cooling to room temperature, the reddish brown liquid reaction product was decanted from salts, the solid residue was washed three times with toluene (30 g), and the washings combined with the liquid products. After removing toluene with vacuum strip, the GC analysis showed that the product contained 61.3% of 2-({2-[2-(dimethylamino)ethoxy]ethyl}methylamino)ethan-1-ol and 35.3% of bis(N,N-2-dimethylaminoethoxyethyl)methylamine.

Example 10

A 1 L four-neck flask was equipped with mechanical stirrer, thermocouple, dropping funnel and reflux condenser connected to a dry-nitrogen source. To the flask was added a mixture of piperazine (86 g, 1 mol) and water (200 g) and was heated to 80° C. with stirring when a homogeneous solution was obtained. A solution of dimethylamino ethyl chloride HCl salt (120 g, 70% solution, 0.83 mol) was added slowly over 1 hour, during which a maximum temperature of 86° C. was achieved. After the addition of the dimethylamino ethyl chloride HCL salt, the reaction mixture was allowed to digest at 80° C. for another five hours. After cooling to 50° C., NaOH (33 g, 0.83 mol) was added and stirred for one hour. Most of the water was stripped from the solution from a short column whereupon precipitate appeared. The mixture was diluted with isopropyl alcohol (IPA) and the yellowish liquids was decanted from solid. The GC-MS analysis showed 52% of the product was dimethylaminoethylpiperazine. Distillation of the liquid with reflux ratio of 2:1 to 5:1 gave the amine product as a fraction boiling at 102-104° C. at 10 torr. The yield was 40 g which amounted to 30% based on the dimethylamino ethyl chloride HCl salt. The resulting product was subjected to GC analysis, which showed over 98% purity.

From the above description, it is clear that the present disclosure is well adapted to carry out the object and to attain the advantages mentioned herein as well as those inherent in the present disclosure. While exemplary embodiments of the present disclosure have been described for the purposes of the disclosure, it will be understood that numerous changes may be made which will readily suggest themselves to those skilled in the art which can be accomplished without departing from the scope of the present disclosure and the appended claims.

The invention claimed is:

1. A method for producing a tertiary amine catalyst comprising reacting a first tertiary amine and a second tertiary amine, wherein:

the first tertiary amine is represented by formula (I):

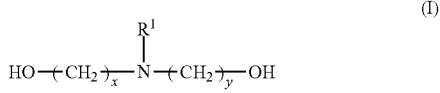
(I)

wherein $R^1$ is selected from a methyl group, an ethyl group, an iso-propyl group, an n-propyl group, and a hydroxyalkyl group selected from a hydroxymethyl group, a hydroxyethyl group, a hydroxypropyl group, and a hydroxyisopropyl group, and x and y independently range from 1 to 4; and the second tertiary amine is represented by formula (II):

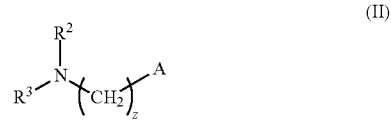
(II)

wherein $R^2$ and $R^3$ are either (i) independently selected from a methyl group, an ethyl group, an iso-propyl group, an n-propyl group, and

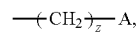

or (ii) linked to form a ring structure having 2 to 8 carbon atoms; z is in a range of from 1 to 4; and A is a halogen.

2. The method of claim 1, wherein $R^1$ is a methyl group and each of x and y is 2.

3. The method of claim 2, wherein $R^2$ and $R^3$ are each methyl groups and z is 2, thereby providing the tertiary amine catalyst comprising at least one of formulas (III) and (IV):

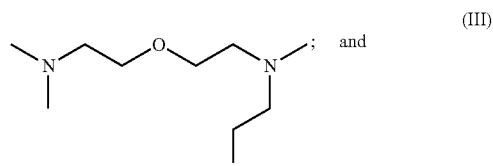
(III)

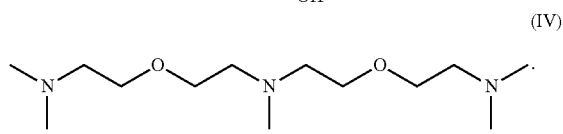
(IV)

4. The method of claim 1, wherein $R^1$ is a hydroxyethyl group and each of x and y is 2.

5. The method of claim 4, wherein $R^2$ and $R^3$ are each methyl groups and z is 2, thereby providing the tertiary amine catalyst comprising at least one of formulas (V), (VI), and (VII):

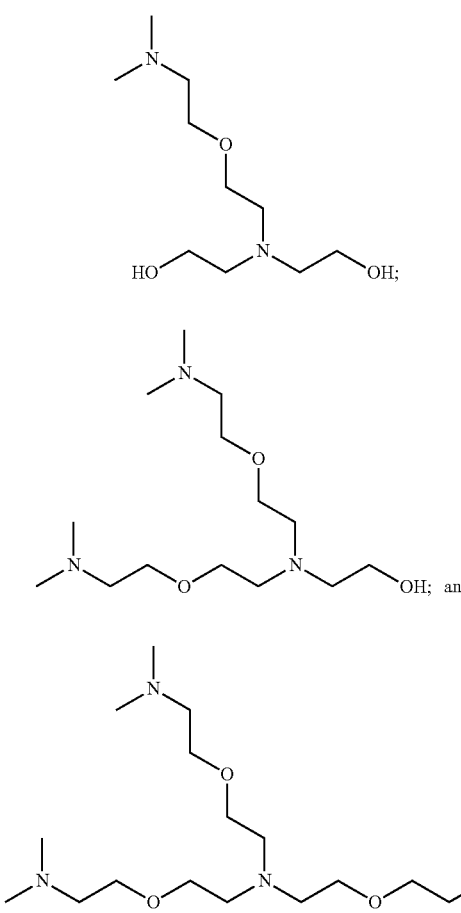

6. The method of claim 1, wherein the first tertiary amine and second tertiary amine are reacted at a temperature in a range of from about 0 to about 150° C. at a pressure ranging from about 1 atm to about 10 atm.

7. The method of claim 6, wherein a molar ratio of the first tertiary amine to the second tertiary amine is in a range of from 1:2 to 1:10.

8. The method of claim 1, wherein the first tertiary amine and the second tertiary amine are reacted in the presence of a base.

9. A method for producing a tertiary amine catalyst comprising reacting a tertiary amine having at least two halogen moieties and a tertiary amine having at least one hydroxyl moiety.

10. The method of claim 9 wherein the tertiary amine having at least two halogen moieties comprises 2-dimethylamino ethyl chloride or a solution thereof.

11. The method of claim 10, further comprising a step whereby the dimethylamino ethyl chloride is formed by reacting methyl diethanol amine and thionyl chloride.

12. The method of claim 9, wherein the tertiary amine having at least one hydroxyl moiety is represented by formula (IX):

$$\text{(IX)}$$

wherein $R^4$ and $R^5$ are independently selected from a methyl group, an ethyl group, an iso-propyl group, and an n-propyl group, and n ranges from 1 to 4.

13. The method of claim 9, wherein the tertiary amine having at least two halogen moieties and a tertiary amine having at least one hydroxyl moiety are reacted in the presence of a base.

14. The method of claim 9, wherein a molar ratio of the tertiary amine having at least two halogen moieties and the tertiary amine having at least one hydroxyl moiety is in a range of from 1:2 to 1:10.

15. The method of claim 14, wherein a molar ratio of the tertiary amine having at least two halogen moieties and the heterocyclic compound comprising an amine and an ether functional group is in a range of from 1:2 to 1:10.

16. A method for producing a tertiary amine catalyst comprising reacting a tertiary amine having at least two halogen moieties and a heterocyclic compound comprising an amine and an ether functional group.

17. The method of claim 16, wherein the tertiary amine having at least two halogen moieties comprises N,N-Bis(2-chloroethyl)methylamine or a solution thereof.

18. The method of claim 17, further comprising a step whereby N,N-Bis(2-chloroethyl)methylamine is formed by reacting methyl diethanol amine and thionyl chloride.

19. The method of claim 17, wherein the heterocyclic compound is morpholine, thereby providing the tertiary amine catalyst represented by formula (X):

$$\text{(X)}$$

20. A method for producing a tertiary amine catalyst comprising reacting piperazine with a tertiary amine having formula (II):

$$\text{(II)}$$

wherein $R^2$ and $R^3$ are either (i) independently selected from a methyl group, an ethyl group, an iso-propyl group, an n-propyl group, and $$-(CH_2)_z-A,$$

or (ii) linked to form a ring structure having 2 to 8 carbon atoms; z is in a range of from 1 to 4; and A is a halogen.

* * * * *